US011109591B2

(12) United States Patent
Van Durme et al.

(10) Patent No.: US 11,109,591 B2
(45) Date of Patent: Sep. 7, 2021

(54) SINGLE PHASE LIQUIDS OF ALKANOLAMINE SALTS OF DICAMBA

(71) Applicant: Taminco BVBA, Ghent (BE)

(72) Inventors: Jim Van Durme, Evergem (BE); Michael Schmidt, Norristown, PA (US); Karen Mollet, Heusden (BE); Kristof Moonen, Hamme (BE); Peter Roose, Deurle (BE)

(73) Assignee: Taminco BVBA, Ghent (BE)

( * ) Notice: Subject to any disclaimer, the term of this patent is extended or adjusted under 35 U.S.C. 154(b) by 475 days.

(21) Appl. No.: 15/957,013

(22) Filed: Apr. 19, 2018

(65) Prior Publication Data

US 2018/0303091 A1  Oct. 25, 2018

Related U.S. Application Data

(60) Provisional application No. 62/488,891, filed on Apr. 24, 2017.

(51) Int. Cl.
| | | |
|---|---|---|
| *A01N 37/40* | (2006.01) | |
| *C07C 253/30* | (2006.01) | |
| *C07C 213/08* | (2006.01) | |
| *C07C 215/08* | (2006.01) | |
| *C07C 217/08* | (2006.01) | |
| *C07C 215/10* | (2006.01) | |
| *C07C 65/21* | (2006.01) | |
| *C07C 51/41* | (2006.01) | |
| *C07F 9/38* | (2006.01) | |
| *A01N 57/20* | (2006.01) | |
| *C07C 59/70* | (2006.01) | |
| *A01N 39/04* | (2006.01) | |
| *C07C 209/68* | (2006.01) | |
| *C07C 211/11* | (2006.01) | |
| *C07C 255/30* | (2006.01) | |
| *A01N 25/02* | (2006.01) | |
| *C07F 9/30* | (2006.01) | |
| *C07C 59/64* | (2006.01) | |

(52) U.S. Cl.
CPC ............ *A01N 37/40* (2013.01); *A01N 25/02* (2013.01); *A01N 39/04* (2013.01); *A01N 57/20* (2013.01); *C07C 51/412* (2013.01); *C07C 59/64* (2013.01); *C07C 59/70* (2013.01); *C07C 65/21* (2013.01); *C07C 209/68* (2013.01); *C07C 211/11* (2013.01); *C07C 213/08* (2013.01); *C07C 215/08* (2013.01); *C07C 215/10* (2013.01); *C07C 217/08* (2013.01); *C07C 253/30* (2013.01); *C07C 255/30* (2013.01); *C07F 9/301* (2013.01); *C07F 9/3808* (2013.01); *C07F 9/3813* (2013.01)

(58) Field of Classification Search
None
See application file for complete search history.

(56) References Cited

U.S. PATENT DOCUMENTS

| | | | |
|---|---|---|---|
| 3,683,010 | A | 8/1972 | Reck et al. |
| 3,852,340 | A | 12/1974 | Reck et al. |
| 4,405,531 | A | 9/1983 | Franz |
| 4,486,356 | A | 12/1984 | Bakel |
| 5,035,738 | A | 7/1991 | Burns et al. |
| 5,175,353 | A | 12/1992 | Jones et al. |
| 5,221,791 | A | 6/1993 | Narayanan et al. |
| 5,266,553 | A * | 11/1993 | Champion ............ A01N 25/12 504/206 |
| 6,133,199 | A | 10/2000 | Soula et al. |
| 6,307,129 | B1 | 10/2001 | Ward et al. |
| 6,455,473 | B2 | 9/2002 | Wright |
| 6,544,930 | B2 | 4/2003 | Wright |
| 6,881,707 | B2 | 4/2005 | Howat et al. |
| 7,022,896 | B1 | 4/2006 | Weeks et al. |
| 7,105,724 | B2 | 9/2006 | Weeks et al. |
| 7,381,861 | B2 | 6/2008 | Cerny et al. |
| 7,632,985 | B2 | 12/2009 | Malven et al. |
| 8,987,167 | B2 | 3/2015 | Xu et al. |

(Continued)

FOREIGN PATENT DOCUMENTS

| | | |
|---|---|---|
| AU | 2007216730 B1 | 1/2009 |
| CA | 936865 A | 11/1973 |

(Continued)

OTHER PUBLICATIONS

Curran, W.S. et al.; Penn State Extension; Agronomy Facts 37; "Adjuvants for Enhancing Herbicide Performance;" http://extension.psu.edu/pests/weeds/control/adjuvants-for-enhancing-herbicide-performance, 2009.
Mueller, Thomas C.; "Methods to Measure Herbicide Volatility;" Weed Science; 63 (spl); pp. 116-120; Published by: Weed Science Society of America; http://www.bioone.org/doi/pdf/10.1614/WS-D-13-00127.1; URL: http://www.bioone.org/doi/full/10.1614/WS-D-13-00127.1, 2015.
Notification of Transmittal of the International Search Report and the Written Opinion of the International Searching Authority dated Jun. 18, 2018 for International Application No. PCT/EP2018/060350.
Behrens et al.; "Dicamba Volatility;" Weed Science; 1979; pp. 486-493; vol. 27; issue 5.

(Continued)

*Primary Examiner* — Abigail Vanhorn
*Assistant Examiner* — Ali S Saeed
(74) *Attorney, Agent, or Firm* — Kenrick L. Vidale

(57) ABSTRACT

The invention is a herbicidal composition containing an alkanolamine salt of an dicamba capable of remaining as a single phase liquid over a period of at least 1 week and containing low amounts of water and high loadings of the salt. Such herbicidal compositions are capable of remaining liquid in the absence of high amounts of water, thereby enhancing their capacity to remain liquid over an extended period of time when exposed to environmental conditions to improve their effectiveness to transport the active salt through a leafy substrate and can reduce transportation costs by increasing the salt loading without compromising the stability of the composition.

1 Claim, 1 Drawing Sheet

(56) References Cited

U.S. PATENT DOCUMENTS

| | | |
|---|---|---|
| 2004/0097372 A1 | 5/2004 | Abraham et al. |
| 2006/0040826 A1 | 2/2006 | Eaton et al. |
| 2006/0270556 A1 | 11/2006 | Wright et al. |
| 2008/0015110 A1 | 1/2008 | Clemente et al. |
| 2008/0028482 A1 | 1/2008 | Beazley et al. |
| 2009/0029891 A1 | 1/2009 | Callahan |
| 2010/0273654 A1 | 10/2010 | Li et al. |
| 2010/0331182 A1* | 12/2010 | Zhang ............... A01N 37/10 504/128 |
| 2011/0210028 A1 | 9/2011 | Zhu |
| 2015/0313212 A1 | 11/2015 | Alexander et al. |
| 2016/0366878 A1* | 12/2016 | Wright .............. A01N 25/22 |

FOREIGN PATENT DOCUMENTS

| | | | |
|---|---|---|---|
| CA | 2008553 A1 | 7/1990 | |
| EP | 0 183 384 A1 | 6/1986 | |
| EP | 0 374 753 A2 | 6/1990 | |
| EP | 0 375 624 A1 | 6/1990 | |
| EP | 0375624 A1 * | 6/1990 | ............ A01N 39/04 |
| EP | 0379 624 A1 | 8/1990 | |
| EP | 0 392 225 A2 | 10/1990 | |
| EP | 0 427 529 A1 | 5/1991 | |
| EP | 0 451 878 A1 | 10/1991 | |
| GB | 1 078 804 A | 8/1967 | |
| GB | 1 339 315 A | 12/1973 | |
| GB | 1339315 A * | 12/1973 | ............ A01N 25/02 |
| WO | WO 91/04661 A2 | 4/1991 | |
| WO | WO 93/07278 A1 | 4/1993 | |
| WO | WO 95/34656 A1 | 12/1995 | |
| WO | WO 97/24931 A1 | 7/1997 | |
| WO | WO 01/26469 A1 | 4/2001 | |
| WO | WO 02/15701 A2 | 2/2002 | |
| WO | WO 02/102153 A2 | 12/2002 | |
| WO | WO 03/018810 A2 | 3/2003 | |
| WO | WO 03/052073 A2 | 6/2003 | |
| WO | WO 2006/023431 A2 | 3/2006 | |
| WO | WO 2006/024820 A1 | 3/2006 | |
| WO | WO 2006/037945 A1 | 4/2006 | |
| WO | WO 2007/071900 A1 | 6/2007 | |
| WO | WO 2007/096576 A1 | 8/2007 | |
| WO | WO 2007/143690 A2 | 12/2007 | |
| WO | WO 2007/143788 A1 | 12/2007 | |
| WO | WO 2008/106107 A1 | 9/2008 | |
| WO | WO 2008/106118 A2 | 9/2008 | |
| WO | WO 2009/068226 A2 | 6/2009 | |
| WO | WO 2009/075591 A1 | 6/2009 | |
| WO | WO 2010/080829 A1 | 7/2010 | |
| WO | WO 2010/123871 A1 | 10/2010 | |
| WO | WO 2011/019652 A2 | 2/2011 | |
| WO | WO 2011/039172 A2 | 4/2011 | |
| WO | WO 2012/040785 A1 | 4/2012 | |
| WO | WO 2012/059494 A1 | 5/2012 | |
| WO | WO 2013/063357 A2 | 5/2013 | |

OTHER PUBLICATIONS

Schubert et al.; "Adjuvants and Volatility of Hormone Herbicides;" Pestic. Sci.; 1993; pp. 179-183; vol. 38.

Tan et al.; "Imidazolinone-tolerant crops: history, current status and future;" Pest Management Science; 61; 2005; pp. 246-257.

Arias et al.; "Molecular evolution of herbicide resistance to phytoene desaturase inhibitors in Hydrilla verticillate and its potential use to generate herbicide-resistant crops;" Pest Management Science; 61; 2005; pp. 258-268.

Li et al.; "Development of PPO inhibitor-resistant cultures and crops;" Pest Management Science; 61; 2005; pp. 277-285.

Matringe et al.; "p-Hydroxyphenylpyruvate dioxygenase inhibitor-resistant plants;" Pest Management Science; 61; 2005; pp. 269-276.

Inui et al.; "Herbicide resistance in transgenic plants with mammalian P450 monooxygenase genes;" Pest Management Science; 61; 2005; pp. 286-291.

Dill et al.; "Glyphosate-resistant crops: adoption, use and future considerations;" Pest Management Science; 64; 2008; pp. 326-331.

Green et al.; "New multiple-herbicide crop resistance and formulation technology to augment the utility of glyphosate;" Pest Management Science; 64; 2008; pp. 332-339.

Green; "Evolution of Glyphosate-Resistant Crop Technology;" Weed Science; 57; 2009; pp. 108-117.

Behrens et al.; "Dicamba Resistance: Enlarging and Preserving Biotechnology-Based Weed Management Strategies;" Science; vol. 316; 2007; pp. 1185-1188.

Invitation to Pay Additional Fees with dated Jun. 27, 2018 for International Application No. PCT/EP2018/060351.

Notification of Transmittal of the International Search Report and the Written Opinion of the International Searching Authority dated Sep. 6, 2018 for International Application No. PCT/EP2018/060351.

Product Safety Assessment DOW N-methyldiethanolamine, Sep. 4, 2014, The DOW Chemical Company, p. 1-6, https://msdssearch.dow.com/PublishedLiteratureDOWCOM/dh_096d/0901b8038096dc16.pdf?filepath=productsafety/pdfs/noreg/233-00470.pdf&fromPage=GetDoc (Year: 2014).

USPTO Office Action dated Sep. 15, 2020 received in co-pending U.S. Appl. No. 15/957,013.

\* cited by examiner

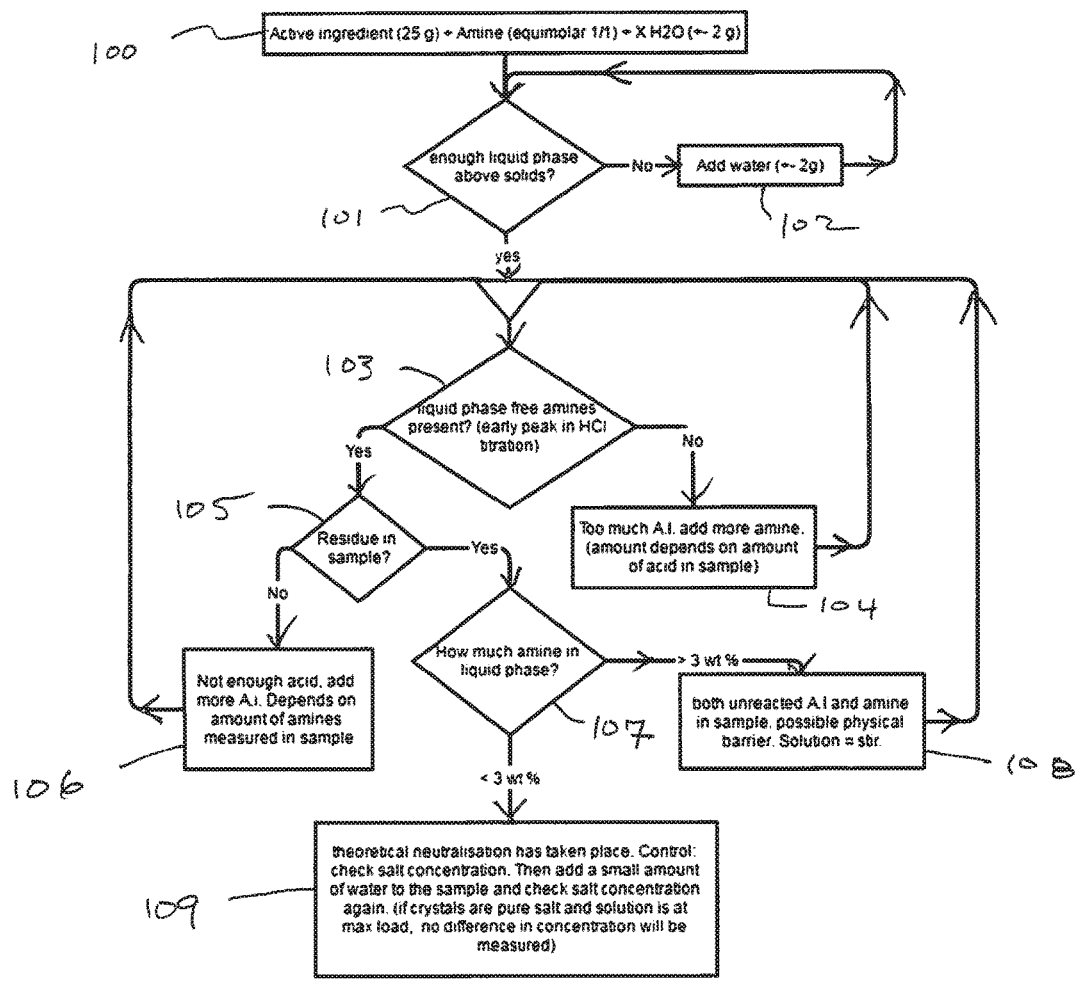

SINGLE PHASE LIQUIDS OF ALKANOLAMINE SALTS OF DICAMBA

CROSS-REFERENCE TO RELATED APPLICATION

This application claims the benefit of U.S. Provisional Application No. 62/488,891 filed on Apr. 24, 2017 under 35 U.S.C. § 119(e)(1); the entire content of the provisional application is hereby incorporated by reference.

FIELD OF THE INVENTION

The invention generally relates to the field of herbicides. The invention particularly relates to certain herbicidal compositions comprising the reaction product of alkanolamine compounds with dicamba.

BACKGROUND OF THE INVENTION

Various herbicide active ingredients have acidic functional groups in their molecular structure. Aqueous-based formulation concentrates may avoid or reduce the need for non-aqueous solvents. When applied in an aqueous formulation, these acid groups can be neutralized with amines to obtain a formulation with the desired pH. Even though some amine-herbicide combinations are commercially available (e.g., ROUNDUP™, BANVEL™ etc.), it would be desirable to increase the maximum loading (g acid/liter formulation) of the active salt, and to improve the efficacy of leaf penetration over time.

Many amine salts of active herbicides, in particular the water soluble salts, are solids and require relatively large amounts of water to provide a liquid composition. The reaction of liquid amines and various carboxylic acid functional herbicides often results in the formation of a two phase system, a lower layer of amine-herbicide salt solids and an upper saturated liquid layer containing water, unreacted amine(s), and/or dissolved amine salts of the herbicide. Increasing the amount of water to the point where all of the solids are solubilized increases transportation costs by having to ship more water. It would be desirable to provide a stable herbicidal composition with a high loading of the amine salt of an herbicide, or a low concentration of solvent, as such a composition would be capable of reducing transportation costs.

It would also be desirable to obtain a composition that, under ambient conditions, is capable of remaining as a single phase liquid over extended periods of time. The efficacy of the amine salts of herbicides on a leafy substrate as measured by diffusion or other transport mechanisms, is impaired once the amine salt solidifies. It would be advantageous to employ an amine salt of an acid functional herbicide that could remain a liquid over extended periods to time at ambient conditions so as to increase the active treatment period of the amine salt of the acid functional herbicide.

The present invention addresses the need for obtaining single phase liquids having high loadings of active amine salts of herbicides and that can remain stable as liquids over extended periods of time.

SUMMARY OF THE INVENTION

There is now provided an herbicidal composition comprising water and an alkanolamine salt, said alkanolamine salt comprising the reaction product of an alkanolamine compound with dicamba, wherein said alkanolamine salt is capable of remaining a single phase liquid for at least 1 week, said capability determined by continuously subjecting the alkanolamine salt to the following test conditions: 2 ml of a sample containing said alkanolamine salt and less than 5 wt. % water, based on the weight of the sample, and no non-aqueous solvents is placed onto a glass surface and exposed to the atmosphere at a temperature within a range of 20° C. to 25° C. and at approximately 1 atmosphere.

There is also provided a process for the preparation of an herbicidal composition comprising:
 a. reacting an alkanolamine compound with dicamba in the presence of water to form a two phase composition comprising a liquid phase and a solid phase, and
 b. exposing the two phase composition to conditions sufficient to form a single phase liquid composition.

There is also provided a process for making an herbicidal composition comprising:
 a. reacting an alkanolamine compound with dicamba in the presence of water to form a two-phase composition comprising a liquid phase and a solid phase, wherein the amount water employed is no more than 10 wt. % water, based on the weight of the two phase composition, and
 b. exposing the two-phase composition to conditions sufficient to form a single phase liquid composition without the addition of more water or with the addition water in an amount such that the single phase liquid composition contains no more than 10 wt. % water based on the weight of the single phase liquid composition.

The composition made by this process is desirably stable for at least 1 week, as measured by the above stated test method.

There is further provided a method for applying an alkanolamine salt of dicamba to a leafy substrate comprising spraying an herbicidal composition onto a leafy substrate, said composition comprising water and salt comprising the reaction product of an alkanolamine compound with dicamba, wherein said salt is capable of remaining a single phase liquid for at least (1) one week, said capability being determined by the above stated test method.

In another embodiment, there is provided a composition containing a reaction product of an alkanolamine with dicamba used as an herbicide for application onto leafy substrates.

There is also provided a method for the sale or offer for sale of an herbicidal composition comprising associating an advertisement or set of instructions with an herbicidal composition, said herbicidal composition comprising the reaction product of an alkanolamine with dicamba, and said advertisement or instructions informing a prospective or actual purchaser of the capability of the herbicidal composition being offered for sale or sold to reduce drift or improve or enhance the active period of the herbicidal composition.

Through investigations to obtain single phase amine salts of carboxylic acid herbicides, we have also discovered two amines which exhibit the ability to form soluble salts at reasonable to high loadings with at least three out of four of the carboxylic acid herbicides tested. While neither of these particular amines formed single phase liquids stable over extended periods of time at ambient temperatures, we have recognized their unique advantage of forming soluble salts with many of the carboxylic acid herbicides at acceptable loading levels, thereby avoiding the necessity of having to use different amines for each different carboxylic acid herbicide. Accordingly, there is also provided a salt comprising 3-(dimethylamino)propionitrile (DMAPN) combined with any one of the four individual carboxylic acid herbicides selected from 2,4-dichlorophenoxyacetic acid (2,4-D), 3,6-dichloro-2-methoxybenzoic acid (dicamba), glufosinate, or glyphosate; and the amine compound 1,2-diaminopropane (1,2-DAP) combined with any one of the three individual carboxylic acid herbicides selected from 3,6-dichloro-2-methoxybenzoic acid (dicamba), glufosinate, or glyphosate. These combinations can form soluble salts at acceptable loadings.

BRIEF DESCRIPTION OF THE DRAWINGS

The FIGURE shows a decision flow chart for preparing herbicide amine salt solutions.

DETAILED DESCRIPTION OF THE INVENTION

It should be understood that the following is not intended to be an exclusive list of defined terms. Other definitions may be provided in the foregoing description, such as, for example, when accompanying the use of a defined term in context.

As used herein, "can" is synonymous with optionally. The terms "a," "an," and "the" mean one or more. The term "and/or," when used in a list of two or more items, means that any one of the listed items can be employed by itself or any combination of two or more of the listed items can be employed. For example, if a composition is described as containing components A, B, and/or C, the composition can contain A alone; B alone; C alone; A and B in combination; A and C in combination, B and C in combination; or A, B, and C in combination. The terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "having," "has," "contain," "including," "includes," "include," and "have" have the same open-ended meaning as "comprising," "comprises," and "comprise" provided above.

The present description uses numerical ranges to quantify certain parameters relating to the invention. It should be understood that when numerical ranges are provided, such ranges are to be construed as providing literal support for claim limitations that only recite the lower value of the range as well as claim limitations that only recite the upper value of the range. For example, a disclosed numerical range of 10 to 100, or within or from 10 to 100, provides literal support for a claim reciting "greater than 10" (with no upper bounds) and a claim reciting "less than 100" (with no lower bounds) and provided literal support for and includes the end points of 10 and 100. It should also be understood that each specific numerical value provided herein is to be construed as providing literal support for any intermediate range and every number within the stated range. The numerical ranges should be applied not only to the specified range values, but should also be applied to data points that are not necessarily expressed as ranges. Thus, if the specification describes a data point of 100 in an example and a second related data point of 48 elsewhere in the specification or other examples, a range of 48 to 100 is described and intended.

Any two numbers of the same property or parameter reported in the working examples may define a range. Those numbers may be rounded off to the nearest thousandth, hundredth, tenth, whole number, ten, hundred, or thousand to define the range.

There is now provided an herbicidal composition comprising water and an alkanolamine salt, said alkanolamine salt comprising the reaction product of an alkanolamine compound with dicamba, wherein said alkanolamine salt is capable of remaining a single phase liquid for at least 1 week, said capability determined by continuously subjecting the alkanolamine salt to the following test conditions: 2 ml of a sample containing said alkanolamine salt and less than 5 wt. % water, based on the weight of the sample, and no non-aqueous solvents is placed onto a glass surface and exposed to the atmosphere at a temperature within a range of 20° C. to 25° C. and at approximately 1 atmosphere. The sample of the alkanolamine salt subjected to the test is not extracted from the herbicidal composition but rather is independently synthesized under the same reaction conditions and recipe used to make the alkanolamine salt in the herbicidal composition, except that the amount of water employed is regulated not to exceed 5 wt. % or the other optional water concentrations described below. If such a sample remains as a single phase liquid to the unaided eye for at least a week under these test conditions, then the herbicidal composition is deemed to contain an alkanolamine salt of dicamba that is capable of remaining a single phase liquid composition regardless of the amount of water or non-aqueous solvent contained in the herbicidal composition. The herbicidal composition may contain any amount of solvent, including water, and any adjuvants. Many amine salts of acid functional herbicides can be single phase liquids when diluted with sufficient water, or non-aqueous solvent, or when aided by surfactants. However, the herbicidal composition of the invention contains a particular salt that, when subjected to a particular set of test conditions, remains as a single phase liquid for at least a week. Employing such a salt has the advantage of both reducing transport costs by utilizing high loadings of the active salt and extending the efficacy of the active herbicide on a leafy substrate by remaining a liquid even when the concentration of water or other solvent is extremely low.

A "single phase liquid" is a homogeneous liquid which does not contain two or more distinct layers when observed with the unaided eye. Behaviors inconsistent with a single phase liquid include liquid/liquid separation of layers, or liquid/solid striation, in each case noticeable as such to the unaided eye. While physical characteristics of compositions can be altered with temperature and pressure, the composition of matter is deemed to be a single phase liquid which, when measured at a temperature within a range of 20 to 25° C. and about 1 atm. pressure, is a homogeneous liquid that does not contain two or more distinct layers as observed with the unaided eye. The single phase liquid need not necessarily be a true solution in the physical sense but will appear to be a single phase to the unaided eye as described above.

Optionally, the single phase liquid also does not contain the presence of solids dispersed throughout the liquid as detected by the unaided eye. For example, the single phase liquid in this case is not an emulsion, suspension, or dispersion, and would not contain two or more layers, in each case as determined by the unaided eye.

The herbicidal composition contains an alkanolamine salt of dicamba that has the capacity of remaining as a single phase liquid in the presence of low amounts of water. The amount of water present is so low that one would expect the alkanolamine salt of dicamba to solidify or crystallize. The herbicidal composition contains an alkanolamine salt of dicamba that has the capacity of remaining as a single phase liquid in the presence of no more than 10 wt. %, or no more than 7.5 wt. %, or no more than 6 wt. %, or no more than 5 wt %, or no more than 4 wt. %, or no more than 3 wt. %, or no more than 2.0 wt. %, or no more than 1.5 wt. %, or no more than 1.0 wt. %, or no more than 0.75 wt. %, or no more than 0.5 wt. %, or no more than 0.25 wt. %, or no more than 0.1 wt. % water based on the weight of the herbicidal composition. The concentration of water in the herbicidal composition may be 1 to 1,000 times, lower than the concentration of water in an oversaturated solution of the reaction product and water.

The herbicidal composition contains an alkanolamine salt of dicamba. Dicamba is 3,6-dichloro-2-methoxybenzoic acid and has the following structure:

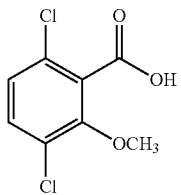 [SMILES: COc1c(Cl)ccc(Cl)c1C(=O)O]

The alkanolamine compound contains at least one hydroxyl group and at least one amine group and contains at least 1 carbon atom, and can be branched or unbranched, saturated or unsaturated, or have at least 3 carbon atoms. Examples of suitable alkanolamines include N-methylaminoethanol (MMEA) and 2-dimethylaminoethanol (DMEA).

The herbicidal composition containing the alkanolamine salt of dicamba can be a formulated composition such as a concentrate, tank mix, or ready to use (RTU) composition. The alkanolamine salt of dicamba can be blended with other ingredients, but because the alkanolamine salt of dicamba can remain a liquid with very low amounts of water, the formulated composition itself can also be formulated with low amounts of water. Thus, there is also provided an herbicidal composition containing an alkanolamine salt of dicamba in a package for sale to the end user, said herbicidal composition obtained by combining ingredients, at least one of said ingredients comprising the reaction product of an alkanolamine with dicamba, and wherein the herbicidal composition contains no more than 10 wt %, or no more than 7.5 wt %, or no more than 6 wt %, or no more than 5 wt. %, or no more than 4 wt %, or no more than 3 wt %, or no more than 2.0 wt %, or no more than 1.5 wt. %, or no more than 1.0 wt. %, or no more than 0.75 wt %, or no more than 0.5 wt %, or no more than 0.25 wt. %, or no more than 0.1 wt. % water based on the weight of the herbicidal composition.

Desirably, the herbicidal composition contains an alkanolamine salt of dicamba that has the capacity of remaining as a single phase liquid in the presence of not only the above described low amounts of water, but also low amounts of non-aqueous solvents. By a solvent is meant a molecule that is inert to the alkanolamine salt of the dicamba and further does not include the reactive raw materials used to make the alkanolamine salt of the dicamba or their by-products. Solvents can be water or non-aqueous molecules.

Optionally, the herbicidal composition is a liquid in the presence of water, wherein the amount of any solvent (water or non-aqueous solvent) is no more than 10 wt. %, or no more than 7.5 wt. %, or no more than 6 wt. %, or no more than 5 wt. %, or no more than 4 wt. %, or no more than 3 wt. %, or no more than 2.0 wt. %, or no more than 1.5 wt. %, or no more than 1.0 wt. %, or no more than 0.75 wt. %, or no more than 0.5 wt. %, or no more than 0.25 wt. %, or no more than 0.1 wt. %, based on the weight of the herbicidal composition.

The herbicidal composition can contain a molar ratio of water to non-aqueous solvent of at least 1:10, or at least 1:2, or at least 1:1, or at least 2:1, or at least 5:1, or at least 10:1, or at least 50:1, or at least 100:1. In one embodiment, no non-aqueous solvents are added to the alkanolamine salt of dicamba. The concentration of water in the herbicidal composition may be 1 to 1,000 times, lower than the concentration of water in an oversaturated solution of the reaction product and water.

The herbicidal composition of the invention is not limited to a particular concentration of solvent. For example, the herbicidal composition of the invention may contain at least 15 wt. %, or at least 20 wt. %, or at least 30 wt. % or at least 50 wt. %, or even 70 or 80 wt. %, or more of water or non-aqueous solvents, provided that such herbicidal composition contains an alkanolamine salt of dicamba that has the capability of remaining a single phase liquid composition as determined by the test method described above. The alkanolamine salts of dicamba employed in the invention have an extended capacity to remain liquid. We have found that an herbicidal composition containing these salts can remain as single phase liquids for extended periods of time, such as for at least one week, or at least two weeks, or at least one month, or at least two months, for at least three months even at low concentrations of solvent. Optionally, the sample can be subjected to a more rigorous test by employing a sample with only up to or about 3 wt. %, or only up to or about 2 wt. % water and no other non-aqueous solvent based on the weight of the sample, and any composition that would pass the more rigorous tests would also be deemed to pass the test at 5 wt. % water.

The alkanolamine salt of dicamba contained in the herbicidal composition is desirably water soluble so that aqueous herbicidal solutions or formulations can be prepared. Accordingly, in various embodiments, the dicamba alkanolamine salts of the invention are water soluble at room temperature or at elevated temperatures (e.g., 40-80° C.) such that they may be formulated in an aqueous solution.

The alkanolamine salts of dicamba are suitable for preparing highly loaded herbicidal solutions, concentrates, and/or emulsion concentrates.

The herbicidal compositions may be in the form of an intermediate suitable for formulating into a formulated composition, or a formulated composition. Examples of formulated compositions include concentrates (also known as pre-mixes), tank-mixes, or ready-to-use (RTU) formulations.

Transportation and storage costs can be minimized by preparing herbicidal compositions in which the loading of the active alkanolamine salt of dicamba is a high as practicable. Desirably, the herbicidal composition comprises at least 500 g a.e./L, or at least 700 g a.e./L, at least 800 g a.e./L, at least 850 g a.e./L, or at least 900 g a.e./L, or at least 1000 g a.e./L total alkanolamine salt of dicamba loading (the "active salt loading"). The samples subjected to the test method described above can also contain any of the above stated loadings, desirably the loadings on the higher end of the range, and even beyond 1000 g a.e./L, such as at least 1100, or at least 1200, or at least 1300 g a.e./L active salt loading.

Tank-mix and RTU formulations comprising one or more of the alkanolamine salts of dicamba would typically comprise from 0.1 g a.e./L to 50 g a.e./L total active salt loading.

The amine compounds 3-(dimethylamino)propionitrile (DMAPN) and 1,2-diaminopropane (1,2-DAP) can form soluble salts at reasonable to high loadings with a variety of individual carboxylic acid herbicides selected from 2,4-dichlorophenoxyacetic acid (2,4-D), 3,6-dichloro-2-methoxybenzoic acid (dicamba), glufosinate, or glyphosate. Examples of suitable active salt loadings include at least 400 g a.e./L, or at least 500 g a.e./L, or at least 600 g a.e./L, or at least 700 g a.e./L, The alkanolamine salt of dicamba is obtained by reacting an alkanolamine compound with dicamba. For example, in one method, the dicamba in free acid form is mixed with an alkanolamine base in water or water combined with other suitable solvents.

The alkanolamine compounds can be in either the protonated or the quaternized form in the herbicide salts of the invention.

Typically, when preparing the alkanolamine salts of dicamba, an equimolar or excess amount of the base may be used. However, when using some alkanolamine compounds that contain more than a single amine functional group (e.g., di- and tri-alkanolamines), equimolar or excess base compound may be unnecessary. Accordingly, in various embodiments, the molar ratio of the alkanolamine compound to dicamba is typically at least 0.4:1, at least 0.5:1, at least 0.6:1, at least 0.7:1, at least 0.8:1, at least 0.9:1, at least 1:1, at least 1.1:1, at least 1.2:1, at least 1.3:1, at least 1.4:1, at least 1.5:1, at least 1.6:1, at least 1.7:1, at least 1.8:1, at least 1.9:1, or at least 2:1. In these and other embodiments, the molar ratio of the alkanolamine compound to dicamba may range from 0.4:1 to 2:1, from 0.5:1 to 2:1, from 0.7:1 to 2:1, from 0.8:1 to 1.8:1, from 0.8:1 to 1.5:1, from 0.9:1 to 1.3:1, from 1:1 to 1.3:1, or from 1.05:1 to 1.3:1.

The reaction between the alkanolamine and dicamba can proceed in the absence of an added catalyst.

The preparation of the alkanolamine herbicidal salt can result in a multi-phase system, one phase being crystallized solids of the alkanolamine salt of dicamba, and another phase being liquid. The two phases can, but need not necessarily be, separated into two layers of their respective phases. In such a case, the liquid layer can contain the solvent, such as water, unreacted alkanolamine compounds, and solubilized alkanolamine salts of dicamba. Alternatively, the composition can contain a solids phase dispersed in the liquid phase, such as would be possible with agitation or shear. One can employ a process for the formation of an herbicidal composition obtained by reacting an alkanolamine with dicamba in the presence of water to form a liquid phase and a solid phase, and with the passage of time, the two phases form a stable single phase liquid. The two phases can spontaneously form the single phase. The two phases are capable of forming a single phase in the presence of low amounts of water as described above, and optionally in the absence of a catalyst.

There is also provided a process for making an herbicidal composition comprising:
a. reacting an alkanolamine compound with dicamba in the presence of water to form a two-phase composition comprising a liquid phase and a solid phase, and
b. exposing the two-phase composition to conditions sufficient to form a single-phase liquid composition.

The first step a) comprises the formation of a two-phase composition comprising a liquid phase and a solid phase, the solid phase comprising the crystallized alkanolamine salt of dicamba and the liquid phase comprising a solution containing the alkanolamine salt of dicamba dissolved in water, followed by a second step b) comprising exposing the two phase composition to conditions sufficient to form a single phase liquid. For purposes of determining whether the composition is single phase liquid in step b), the composition is viewed at a temperature within a range of 20° C. to 25° C. and 1 atmosphere as a single phase with the unaided eye. This particular method is to be distinguished from the method of determining whether a particular alkanolamine salt of dicamba is capable of remaining as a single phase liquid for an extended period of time, e.g. 1 week or more.

The formation of the single-phase, liquid composition in step two occurs by exposing the two phase composition to a temperature and pressure for a time sufficient to form the single-phase, liquid composition. The two-phase composition may be in the form of a liquid and solid layer, or a dispersion of solids in liquid. The exposing step can be as simple as time with no agitation or addition of any other ingredients, or can be accelerated with increased temperature and/or reduced pressure optionally under agitation or with the addition of surfactants. The exposing step can be carried out in a closed vessel if desired. Suitable preparation temperatures and pressures are not particularly limited provided that the conditions are conducive to the formation of the single phase liquid herbicidal salt composition. Examples of suitable preparation temperatures range from 10° C. to 60° C. The time sufficient to form the single-phase, liquid composition may vary, depending on the particular alkanolamine-dicamba combination and the application of mechanical agitation, temperature and pressure. For example, the time may be one 1 hour, 1 day, one week, or two weeks or more. This time may be reduced by using elevated temperatures and/or reduced pressures.

The single phase composition is capable of forming a single phase without the addition of high amounts of water. For example, there is also provided a process for making an herbicidal composition comprising:
a. reacting an alkanolamine compound with dicamba in the presence of water to form a two-phase composition comprising a liquid phase and a solid phase, wherein the amount water employed is no more than 10 wt. % water, based on the weight of the two-phase composition, and
b. exposing the two-phase composition to conditions sufficient to form a single phase liquid composition without the addition of more water or with the addition water in an amount such that the single phase liquid composition contains no more than 10 wt. % water based on the weight of the single phase liquid composition.

In this process embodiment, the amount of water in any one of or both of steps a) and b) can be no more than 7.5 wt. %, or no more than 6 wt. %, or no more than 5 wt %, or no more than 4 wt %, or no more than 3 wt. %, or no more than 2.0 wt. %, or no more than 1.5 wt. %, or no more than 1.0 wt. %, or no more than 0.75 wt. %, or no more than 0.5 wt. %, or no more than 0.25 wt. %, or no more than 0.1 wt. %

By employing this process, the single-phase liquid composition can be transported with high active salt loadings, thereby reducing transportation costs. Further, a single-phase liquid can be formed in the first instance with low amounts of water without incurring additional process steps and energy to remove high amounts of water to achieve the high loadings obtainable in the invention.

In both processes, the two phase liquid composition can optionally spontaneously form a single phase liquid from a two phase composition containing a liquid phase and a solid phase, meaning that while agitation, time, and/or mechanical manipulations can be employed, the solid alkanolamine salt of the dicamba is capable of forming a single phase liquid without the use of added processing aids or surfactants, other than reaction ingredients. For example, in one embodiment, from a two phase composition of a liquid phase and a solid phase, a single phase liquid composition containing an alkanolamine salt of dicamba is formed without the addition of surfactants, dispersing aids, and/or wetting agents, and optionally after a single phase liquid composition is formed, surfactants, dispersing aids, and/or wetting agents can be optionally added.

The herbicidal compositions can be a gel, a pourable liquid at 22° C./1 atm., and can be transparent, translucent, or opaque.

If desired, the herbicidal composition may also contain, in addition to the dicamba salts, the salts of other acidic herbicides that are Bronsted-Lowry acids or a Lewis acids. Such additional herbicides desirably contain at least one proton donating group, such as a carboxylic acid group. The optional additional acidic herbicides may contain two or more acid moieties, which can be the same or different, such as two or more carboxylic acid groups or a carboxylic acid group and a phosphoric acid group, or desirably at least one proton donating group, or at least one carboxylic acid moiety, or in salt form, a carboxylate anion.

Examples of other acidic herbicides include 2,4-dichlorophenoxyacetic acid (2,4-D); 4-(2,4-dichlorophenoxy)butanoic acid (2,4-DB); glufosinate, glufosinate-P, glyphosate, 2-(2,4-dichlorophenoxy)propanoic acid (dichloroprop); 2-(4-chloro-2-methylphenoxy)acetic acid (MCPA); 4-(4-chloro-2-methylphenoxy)butanoic acid (MCPB); 4-amino-3,6-dichloro-2-pyridinecarboxylic acid (aminopyralid); 3,6-dichloro-2-pyridinecarboxylic acid (clopyralid); 2-[(4-amino-3,5-dichloro-6-fluoro-2-pyridinyl)oxy] acetic acid (fluroxypyr); [(3,5,6-trichloro-2-pyridinyl)oxy] acetic acid (triclopyr); 2-(4-chloro-2-methylphenoxy)propanoic acid (mecoprop); 4-amino-3,5,6-trichloro-2-pyridinecarboxylic acid (picloram); 3,7-dichloro-8-quinolinecarboxylic acid (quinclorac); 6-amino-5-chloro-2-cyclopropyl-4-pyridinecarboxylic acid (aminocyclopyrachlor), or combinations thereof.

The herbicidal composition according to the invention can be particularly advantageous when compared with conventional amine-herbicide salts, because it can remain in active form (i.e., liquid) longer than conventional amine-herbicide salts. As such, the single-phase, liquid composition can have a longer and/or more potent effect on the treated plant even as excess water evaporates in exposed atmospheric field conditions because of their capability of remaining liquid with extremely low amount of water.

The herbicidal composition may be formulated into long-lasting or long-acting herbicidal formulations (such as concentrates, tank-mixes, and ready-to-use (RTU) formulations) when blended with conventional adjuvants, excipients, and/or additives.

The alkanolamine salts of dicamba may be formulated with conventional adjuvants, excipients, and/or additives. For example, the salts can be combined with a selection of adjuvants to enhance one or more of the salts' properties. Adjuvants are commonly used in agriculture to improve the performance of the active herbicide. Broadly defined, "an adjuvant is an ingredient that aids or modifies the action of the principal active ingredient."

The use of adjuvants with agricultural chemicals generally falls into two categories: (1) formulation adjuvants are present in the container when purchased by the dealer or grower; and (2) spray adjuvants are added along with the formulated product to a carrier such as water. The liquid that is sprayed over the top of a crop, weeds, or insect pest often will contain both formulation and spray adjuvants.

Formulation adjuvants may be added to the active salt ingredient for several reasons, including better mixing and handling, increased effectiveness and safety, better distribution, and drift reduction. These traits are accomplished by altering the solubility, volatility, specific gravity, corrosiveness, shelf-life, compatibility, or spreading and penetration characteristics. With the large number of formulation options available (solutions, emulsions, wettable powders, flowables, granules, and encapsulated materials), adjuvants can be advantageous in assuring consistent performance.

Literally hundreds of chemical additives are now available that fall into the category of spray adjuvants. Spray adjuvants can be grouped into two broad categories: (1) activator adjuvants, including surfactants, wetting agents, stickers-spreaders, and penetrants; and (2) special purpose or utility modifiers, such as emulsifiers, dispersants, stabilizing agents, coupling agents, co-water, compatibility agents, buffering agents, antifoam agents, drift control agents, and nutritionals.

Other additives or ingredients may be introduced into the compositions of the present invention to provide or improve certain desired properties or characteristics of the formulated product. Thus, the herbicidal composition may further comprise one or more additional ingredients, such as surfactants, foam-moderating agents, preservatives or antimicrobials, antifreeze agents, solubility-enhancing agents, dispersants, stabilizers, dyes, and thickening agents. For example, in various embodiments, the herbicidal composition comprising an herbicidal salt of the invention, may further comprise a surfactant selected from the group consisting of alkoxylated tertiary etheramines, alkoxylated quaternaryetheramines, alkoxylated etheramine oxides, alkoxylated tertiary amines, alkoxylated quaternary amines, alkoxylated polyamines, sulfates, sulfonates, phosphate esters, alkyl polysaccharides, alkoxylated alcohols, and combinations thereof. The weight ratio of the carboxylic acid herbicide amine salt acid equivalent to surfactant can be readily determined by those skilled in the art (e.g., from 1:1 to 20:1, from 2:1 to 10:1 or from 3:1 to 8:1).

There is further provided a method for applying an alkanolamine salt of dicamba to soil or to a leafy substrate comprising spraying an herbicidal composition onto the soil or leafy substrate, said composition comprising water and salt comprising the reaction product of an alkanolamine compound with dicamba, wherein said salt is capable of remaining a single phase liquid for at least (1) one week, said capability being determined by the above stated test method.

Herbicidal compositions that are suitable for application onto a leafy substrate may be prepared by dissolving the salts in water or other suitable solvent or by suitable dilution of a concentrate composition, optionally containing adjuvants, and applying to the foliage of unwanted plants by methods known in the art. A leafy substrate is the foliage on a plant, and can include grasses and canes. The application mixture can be applied to the foliage of a plant or plants at an application rate sufficient to give a commercially acceptable rate of weed control. This application rate is usually expressed as amount of herbicide per unit area treated, e.g., grams acid equivalent per hectare (g a.e./ha). Depending on plant species and growing conditions, the time required to achieve a commercially acceptable rate of weed control can be as short as a week or as long as three weeks, four weeks, or 30 days. Application mixtures of the herbicides salts can be applied before planting, at planting, pre-emergence, or post-emergence to crop plants depending on the particular herbicide salt and crop plant.

The herbicidal compositions prepared with the herbicide salts of the invention may be applied to the foliage of crop plants and/or unwanted plants in the proximity of crop plants. Crop plants include hybrids, in-breeds, and transgenic or genetically modified plants having specific traits or combinations of traits including, without limitation, herbicide tolerance (e.g., tolerant to carboxylic acid herbicides or other herbicides), *Bacillus thuringiensis* (Bt), high oil, high lysine, high starch, nutritional density, and drought resistance. Particular crop plants include, for example, corn, peanuts, potatoes, soybeans, canola, alfalfa, sugarcane, sugar beets, peanuts, grain sorghum (milo), field beans, rice, sunflowers, wheat and cotton. In various embodiments, the crop plant can be soybeans, cotton, peanuts, rice, wheat, canola, alfalfa, sugarcane, sorghum, and sunflowers. In other embodiments, the crop plant can be corn, soybean, and cotton.

Herbicidal compositions containing an herbicide salt of the invention can be applied pre-planting of the crop plant to the soil, such as from two to three weeks before planting. The application mixture can be applied at planting, pre-emergence, or post-emergence to crop plants to control weeds in a field of the crop plants.

The alkanolamine salts of dicamba find particular use in herbicidal compositions, especially for those where extended activity of the active herbicide is desired.

Given the efficacy of the alkanolamine salts of dicamba toward extending the active period of the salt, there is also provided a method for the sale of an herbicidal composition in which an advertisement or set of instructions is associated with an herbicidal composition, said herbicidal composition comprising the reaction product of an alkanolamine with dicamba, and said advertisement or instructions informing the purchaser of the herbicidal composition of the capability of the herbicidal composition to reduce drift or improve or enhance the active period of the herbicidal composition. For example, the label on a package containing the herbicidal composition of the invention can advertise any one of the beneficial features described herein to the purchaser, or instruct the purchaser to treat the crops or leafy substrates in accordance with the capacity of the herbicidal composition to remain as a liquid for an extended period of time once applied to the leafy substrates. The purchaser can be an actual or prospective purchaser. The advertisement or instruction can be including with the packaging containing the herbicidal composition, or may only refer to the herbicidal composition which may be provided at an earlier or later date to the purchaser. The herbicidal composition can be sold in totes, rail cars, small plastic containers (e.g. 25 liters or less), or any other suitable packaging, and may be sold by the manufacturer of the active salt to a formulator, by a formulator to its customers, or at a wholesale or retail level.

Optionally, the herbicidal alkanolamine salts of the invention can exhibit, simultaneously with lower concentrations of water and high loading capacity, other enhanced properties including one or more of lower volatility, wettability, drift reduction, and acceptable viscosity profiles.

While not wishing to be bound by theory, volatility is a known problem of application mixtures containing salts of many carboxylic acid herbicides. Volatility of the acid herbicides is correlated to the free acid concentration in the aqueous solution. As the amine salting agent volatilizes from solution, the free acid concentration increases resulting in higher volatility of the herbicide. In some instances, the amine salts of the present invention could provide desirable low volatility through, for instance, increased amine molecular weight or hydrogen bond acceptance, keeping the amine in solution. A more stable amine concentration in solution results in reduced free acid herbicide in solution and reduced associated offsite movement.

The present invention includes and expressly contemplates any and all combinations of embodiments, features, characteristics, parameters, and/or ranges disclosed herein. That is, the invention may be defined by any combination of embodiments, features, characteristics, parameters, and/or ranges mentioned herein.

It is contemplated that any ingredient, component, or step that is not specifically named or identified as part of the invention may be explicitly excluded by at least some embodiments of the invention.

Any process, apparatus, compound, composition, embodiment, or component of the invention may be modified by the transitional terms "comprising," "consisting essentially of," or "consisting of," or variations of those terms.

As used herein, the terms "acid equivalent," "a.e.," or "ae" refer to the amount of herbicide present without taking into account the weight of the alkanolamine counter-ion of the salt species present.

The content of all documents cited herein, including patents as well as non-patent literature, is hereby incorporated by reference in their entirety. To the extent that any incorporated subject matter contradicts with any disclosure herein, the disclosure herein shall take precedence over the incorporated content.

This invention can be further illustrated by the following examples of preferred embodiments thereof, although it will be understood that these examples are included merely for purposes of illustration and are not intended to limit the scope of the invention.

As may be seen from the following examples, the herbicidal alkanolamine salts of the present invention can solve one or more of the following technical problems:

High-loaded concentrates being highly (physical and chemical) stable during storage.

High-loaded concentrates being easily diluted in water.

Formed salts remaining as single phase liquids over an extended period of time in the presence of low concentrations of solvent, thus ensuring an improved uptake and longer efficacy grade.

Reduced sensitivity of innovative concentrates to drift compared to currently commercially available competitive products.

Unique wettability properties of the innovative concentrates.

EXAMPLES

Salt Preparation

To efficiently prepare a salt, the method, shown as a flowchart in The FIGURE, has been developed.

Referring to The FIGURE, step 100 involves using a mass balance to weigh 25 g of the active ingredient (a solid acidic herbicide, such as 2,4-D, dicamba, glufosinate, or glyphosate) in a glass bottle. An equimolar amount of a basic amine (typically a liquid) is added to this glass bottle. Last, 2 mL of water is added. After adding the three compounds, the bottle is capped and placed on an shaking device for at least 12 hours.

After the mixing/shaking period, at step 101, the system is visually evaluated. If a solid or sludge is formed, step 102 is commenced. If a clear layer is present, step 103 is commenced.

In step 102, the glass bottle is opened and 2 mL of water is added. The system is capped again and placed on a shaking device for 12 hours. Step 101 is then repeated.

At step 103, a small fraction of the liquid top layer is withdrawn to determine the free amine content. 0.1 N HCl is used as a titrant, and methanol is used as a solvent. Conductometry is used for detection. When analyzing samples, the designated amount of sample weighed should be around 100-400 mg, so that about 10-20 mL of the titrant is used. The result is given in an EP (=Equivalence point in titration curve). The following calculation is used to obtain the amine wt %:

$$\text{wt \%}_{amine} = \frac{EP * MM_{amine}}{1000}$$

If no amines are detected, go to step 104. If amines are detected, go to step 105.

The absence of amines in step 103 means that there is probably still unreacted acidic herbicide present in the system. To ensure that all herbicides are neutralized and converted into a salt, a small amount of amines (e.g., 5% of the original amount added) should be added at step 104. After shaking the enriched glass system for 12 hours, the liquid phase is reevaluated at step 103.

At step 105, a visual inspection of the system is conducted. The goal is to obtain a two-phase system containing salt solids and a saturated liquid top layer. If no salt solids are seen, then step 106 is performed. If salt solids can be seen, then step 107 is performed.

At step 106, if no salt solids are visible and free amines are still present, then additional acidic herbicide is introduced into the system (e.g., 5% of the original amount added). After shaking the enriched glass system for 12 hours, the liquid phase is reevaluated at step 103.

At step 107, the amount of free amines in the liquid top layer is calculated based on the titration results. If the calculated amount is 3 wt % or more, then step 108 is performed. If the calculated amount is less than 3 wt %, then step 109 is performed.

At step 108, the high amine concentration in the top layer may indicate that a complete neutralization reaction did not occurred. This may be due to poor mixing (e.g., due to crust formation) and that more intensive stirring is required (e.g., with a spoon, stir bar, or ultrasound). After physically breaking the crust and mixing the two phases, the system should be shaken for at least 12 hours. Then, step 103 is repeated.

At step 109, theoretical neutralization has taken place. The salt concentration can be quantified by titration. To confirm that the solid layer is solid salt and the top layer is a saturated (max. loading) solution, a small amount of water is added (the amounts of water should be small enough to avoid a complete dissolution of the solid salt). After re-equilibrium during at least 12 hours of shaking, and under the condition that two phases are still present, the salt concentration is determined again. If salt concentrations are identical as the original values, then it can be concluded that a maximum loaded solution was obtained.

The flow chart in The FIGURE is based on (a) measuring the pH of the obtained liquid layer (too high a pH indicates the presence of unreacted amines), and/or (b) measuring the free amine content in the liquid. If neutralization is insufficient, increased stirring or placing the system is an ultrasonic bath may be required. These techniques should ensure mixing of the two reactants (amine and herbicide), until neutralization.

By using the decision flowchart, the following errors in making the salts can be avoided:

The evaluated liquid layer containing unreacted amines, thereby not fully neutralizing the added herbicide (due to poor mixing, formation of an impermeable salt layer, etc.).

The residual solid layer in the system containing unreacted herbicide, instead of salt crystals.

The resulting salt solution may contain suspended salt crystals. In which case, the solution can be deemed to be oversaturated.

Analysis of the Max Load Solutions

To determine maximum loading of the salt in water, the method shown in the flowchart of The FIGURE was used. The resulting sample contained at least two layers: a top layer of liquid and a bottom layer of solid salt. A water and amine determination was made of the top layer.

Water Content

To check the water content, a well-established method of Karl-Fischer was used. This method gives an accurate wt % of $H_2O$ in the sample.

Amine Content

To determine the amine content, HCl-titration was used. HCl (0.1 N) was used as the titrant, and methanol was used as the solvent. 100-400 mg of the sample was taken from the liquid layer so that only 10-20 mL of the titrant was needed. The result was given in an EP. The following calculation was used to obtain the amine wt %:

$$\text{wt \%}_{amine} = \frac{EP * MM_{amine}}{1000}$$

wherein $MM_{amine}$ is the molecular weight of the amine.

In general, the sample's liquid phase only contains three components: water, free amine, and the herbicide salt. Therefore, the following calculation was used to determine the salt wt %:

$$\text{wt \%}_{salt} = 1 - \text{wt \%}_{amine} - \text{wt \%}_{water}$$

The results below are reported in g a.e./L (acid equivalent). This represents the amount in g of active herbicide in the sample (it does not represent the amount of functional acid groups on the herbicides molecule). The results were calculated using the following equation:

$$g_{ae}/l = \frac{\text{wt \%}_{salt}}{MM_{acid} + (MM_{amine} * F)} (MM_{acid}) * \rho * 1000$$

The MMs in the equation above are molecular weights (g/mol). $\rho$ is the density of the liquid (g/mL), which may be measured using the density meter Anton Paar DMA 4500. F is a factor that takes into account the amount of base or acid groups on the amine or acid, respectively.

The g amine/l reported below was calculated using the following equation:

$$g_{amine}/l = \frac{\text{wt \%}_{salt}}{MM_{acid} + (MM_{amine} * F)} (MM_{amine} * F) * \rho * 1000$$

Viscosity

The viscosity of the solutions prepared as above was determined using the Brookfield nr. 87 spindle. The applied speed depended on the viscosity of the sample. The torque applied was 50-80% of the machine's maximum. The results are expressed as mPa.

Example 1

Preparation of High-Loaded Dicamba Amine Salt Solutions 25.02 g of dicamba herbicide was mixed with 4.16 g of 1,2-DAP and 5.88 g of water. The ingredients were shaken for a minimum of 24 hours at room temperature (20° C.) to obtain an oversaturated salt solution (with precipitated salt crystals). Theoretically, 1 mol of dicamba can be neutralized using 0.5 mol of 1,2-DAP. Water was gradually added until all the salt crystals were dissolved to form a maximum loaded clear solution. The loading of the active ingredient was determined based on the amine content by HCl titration and the water content by Karl-Fischer.

Maximum loading of 803.2 g ae/L herbicide and 365.9 g amine/L were measured. The loadings are in line with a control salt made of DGA with dicamba.

Similar experiments were performed for other amines in combination with dicamba. The other amines and the results are shown in Table 1.

TABLE 1

Maximum Loadings of Dicamba Amine Salts

| Amine | | Max Load | |
|---|---|---|---|
| Name/Structure | Abbreviation | g ae/L | amine g/L |
|  dimethylamine | DMA | 1036.8 | 211.1 |
| 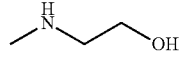 2-methylaminoethanol | MMEA | 928.8 | 357.7 |
| 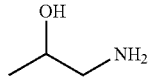 1-amino-2-propanol | amino-2-prop | 883.3 | 352.3 |
| 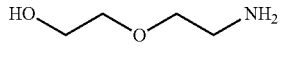 diglycolamine | DGA | 854.9 | 435.5 |
| 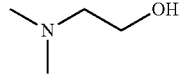 dimethylaminoethanol | DMEA or DMAE | 849.0 | 408.3 |
| 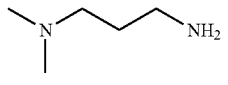 Dimethylaminopropylamine | DMAPA | 827.3 | 349.0 |
| potassium hydroxide | KOH | 827.2 | 225.5 |
| 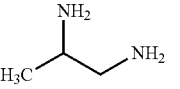 1,2-diaminopropane | 1,2-DAP | 803.2 | 365.9 |
| 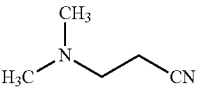 3-(dimethylamino)propionitrile | DMAPN | 775.6 | 443.5 |
| 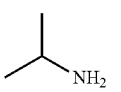 Isopropylamine | MIPA | 765.2 | 309.1 |
| 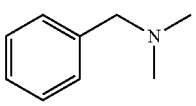 Benzyldimethylamine | BDMA | 729.2 | 486.3 |
| 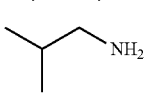 Isobutylamine | MIBA | 713.7 | 475.0 |
| 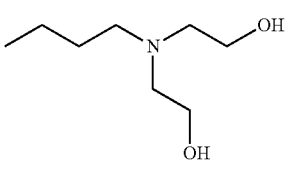 Butyldiethanolamine | BDEA | 659.0 | 519.7 |
| 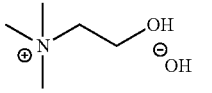 choline hydroxide | Cbase | 481.5 | 308.5 |
| 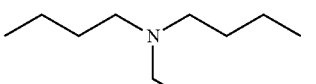 tri-n-butylamine | TNBA | 368.2 | 728.2 |

Example 2

Preparation of High-Loaded 2,4-D Amine Salt Solutions

Using the same methodology as described in Example 1, high-loaded 2,4-D salt solutions were prepared. The amines used and the results are shown in Table 2.

TABLE 2

Maximum loadings of 2,4-D Amine Salts

| Amine | Max Load | |
|---|---|---|
| | g ae/L | amine g/L |
| DMA | 936.1 | 264.4 |
| DMAPA | 863.5 | 210.6 |
| DMAPN | 809.0 | 401.3 |
| MIPA | 801.1 | 216.2 |
| MMEA | 774.3 | 302.5 |
| BDMA | 697.9 | 549.2 |
| DGA | 693.5 | 351.2 |
| KOH | 692.8 | 224.9 |
| DMEA | 624.7 | 316.9 |
| BDEA | 617.7 | 577.0 |
| MDIPA | 596.8 | 519.6 |
| TNBA | 570.3 | 496.3 |
| MIBA | 497.8 | 183.5 |
| Cbase | 195.0 | 315.6 |
| amino-2-prop | 180.0 | 149.5 |

Example 3

Preparation of High-Loaded Glyphosate Amine Salt Solutions

Using the same methodology as described in Example 1, high-loaded glyphosate salt solutions were prepared. The amines used and the results are shown in Table 3.

TABLE 3

Maximum Loadings of Glyphosate Amine Salts

| Amine | Max load | |
|---|---|---|
| | g ae/L | amine g/L |
| DMA | 551.6 | 572.0 |
| MIPA | 551.6 | 416.2 |
| KOH | 505.5 | 382.9 |
| DMAPN | 500.4 | 310.2 |
| Cbase | 452.4 | 719.8 |
| DMEA | 436.7 | 680.5 |
| 1,2-DAP | 434.2 | 205.5 |
| MIBA | 397.2 | 541.8 |
| MMEA | 374.3 | 767.2 |
| BDMA | 365.1 | 583.9 |
| amino-2-prop | 326.9 | 616.8 |
| TNBA | 242.9 | 563.3 |
| DGA | 229.4 | 363.4 |
| BDEA | 189.5 | 883.3 |

Example 4

Preparation of High-Loaded Glufosinate Amine Salt Solutions

Using the same methodology as described in Example 1, high-loaded glufosinate salt solutions were prepared. The amines used and the results are shown in Table 4.

TABLE 4

Maximum Loadings of Glufosinate Amine Salts

| Amine | Max Load | |
|---|---|---|
| | g ae/L | amine g/L |
| 1,2-DAP | 587.1 | 312.3 |
| DMAPA | 587.0 | 401.7 |
| DMAPN | 539.8 | 392.6 |
| MIBA | 417.1 | 425.4 |
| DMEA | 393.8 | 534.9 |
| amino-2-prop | 387.6 | 606.8 |
| BDMA | 376.1 | 581.9 |
| MMEA | 238.6 | 705.3 |
| MIPA | 305.7 | 492.4 |
| $NH_3$ | 1339 | 1340 |

As can be seen from the data of Examples 1, 2, 3, and 4, (dimethylamino)propionitrile (DMAPN) formed a soluble salt at reasonable (at least 400 g ae/L) to high loadings with at any of the four individual carboxylic acid herbicides 2,4-dichlorophenoxyacetic acid (2,4-D), 3,6-dichloro-2-methoxybenzoic acid (dicamba), glufosinate, or glyphosate. Further, the Examples 1, 3 and 4 demonstrate that amine compound 1,2-diaminopropane (1,2-DAP) formed soluble salts at reasonable (at least 400 g ae/L) to high loadings with any of the three individual carboxylic acid herbicides 3,6-dichloro-2-methoxybenzoic acid (dicamba), glufosinate, or glyphosate.

Example 5

The amine-herbicide formulations prepared in Examples 1, 2, 3, and 4 were stored in closed containers at ambient conditions (room temperature varying from 20-25 C, atmospheric pressure) for several months. At the end of several months, five amine-herbicide combinations formed single phase liquids in that no visual presence of the salt solids was detected. The liquefied combinations and the densities of their max-load solutions at ambient temperature in parentheses were MMEA/dicamba (1.31 g/cm$^3$), DMAE/dicamba (1.27 g/cm$^3$), DMAPA/dicamba (1.27 g/cm$^3$), BDMA/2,4-D (1.25 g/cm$^3$), and TNBA/2,4-D (1.1 g/cm$^3$). All five samples contained no more than 5 wt % water based on the weight of the herbicidal composition, thereby allowing for higher concentrations of active herbicide and improved transportability. The five single phase liquid samples did not require surfactants or dispersant aids to obtain the liquid compositions.

To evaluate the herbicidal compositions under more stringent conditions, we increased their surface area and exposed them to ambient conditions at room temperature, atmospheric pressure, and uncovered over an extended period of time: 2 mL samples of the five liquefied combinations were spotted onto glass plates and left uncovered at ambient conditions (temperatures within a range of 20°-25° C.) for approximately two months. After which time, the samples of DMAPA/dicamba, BDMA/2,4-D, and TNBA/2,4-D had turned into a crystallized mass. However, the samples of MMEA/dicamba and DMAE/dicamba remained liquefied even after two months under ambient conditions. These particular samples would have extended life stability at ambient conditions after atmospheric exposure such as would be the case upon and after field application to leaf substrates.

Unless otherwise indicated, all percentages above are in weight based on the total weight of the composition.

The invention has been described in detail with particular reference to preferred embodiments thereof, but it will be understood that variations and modifications can be effected within the spirit and scope of the invention.

We claim:

1. A salt comprising obtained by combining an amine and a carboxylic acid herbicide;
   wherein the amine comprises 3-(dimethylamino)propionitrile (DMAPN) and the herbicide comprises 2,4-dichlorophenoxyacetic acid (2,4-D), 3,6-dichloro-2-methoxybenzoic acid (dicamba), glufosinate, or glyphosate.

* * * * *